United States Patent [19]

Upchurch

[11] Patent Number: 4,846,218

[45] Date of Patent: Jul. 11, 1989

[54] CHECK VALVE FOR LIQUID CHROMATOGRAPHY PUMPS

[76] Inventor: Paul E. Upchurch, 2082 West Pinewood Way, Oak Harbor, Wash. 98277

[21] Appl. No.: 202,215

[22] Filed: Jun. 3, 1988

[51] Int. Cl.[4] ............................................ F16K 15/04
[52] U.S. Cl. .................. 137/544; 137/269.5; 137/512; 137/533.11; 137/550; 210/136; 210/198.2
[58] Field of Search ............... 137/269.5, 454.4, 454.5, 137/512, 533.11, 533.13, 533.15, 544, 550; 210/136, 198.2

[56] References Cited

U.S. PATENT DOCUMENTS

| | | | |
|---|---|---|---|
| 3,661,167 | 5/1972 | Hussey | 137/269.5 |
| 3,810,716 | 5/1974 | Abrahams et al. | 137/533.11 X |
| 4,045,343 | 8/1977 | Achener et al. | 210/198.2 X |
| 4,139,469 | 2/1979 | Rainin et al. | 137/512 X |
| 4,282,897 | 8/1981 | De Mey | 137/512 X |
| 4,387,736 | 6/1983 | Major | 137/512 |
| 4,636,316 | 1/1987 | Harris et al. | 210/198.2 X |

*Primary Examiner*—Gerald A. Michalsky
*Attorney, Agent, or Firm*—Seed and Berry

[57] ABSTRACT

A check valve with a disposable filter is provided for regulating the flow of a mobilizing liquid in a pump of a liquid chromatograph. The valve assembly includes two seated ball valve subassemblies securely housed in a casing to define a liquid flow path therethrough. A portion of one valve subassembly extends beyond the valve casing and is received by a valve end cap. The valve end cap has an aperture which is aligned with the flow path defined by the valve subassemblies. The apertured end of the end cap has a tapered perimeter for receiving a correspondingly tapered end seal. The end seal has an apertured end wall with a filter received in the aperture and is adapted to be removably mounted on the tapered edge of the end cap, thereby removably mounting the filter to the valve assembly and requiring only the force of the user's fingers to attach and remove the filter.

7 Claims, 1 Drawing Sheet

4,846,218

CHECK VALVE FOR LIQUID CHROMATOGRAPHY PUMPS

TECHNICAL FIELD

The present invention concerns pumps for use in liquid chromatography and, more particularly, a disposable check valve assembly for liquid chromatography pumps.

BACKGROUND OF THE INVENTION

Liquid chromatography has been known in the art as a process for determining the composition of various materials for several years. Using this procedure, a test material is added to a liquid mobilizer and passed through a stationary liquid or solid phase material under extremely high pressures. The test material emanates from the solid phase material in a separated fashion such that the relative quantities of its component substances can be measured. The high pressure needed for liquid chromatography creates a need for precision instruments to control the pressure of the fluid flow.

The check valve assemblies used in liquid chromatography pumps must therefore be carefully monitored and often replaced to maintain the necessary precision required for their application. Additionally, filters are generally used with the valve assemblies, which filters must be replaced more often than the assemblies themselves.

Prior art valve assemblies used with liquid chromatograph pumps are generally made to be disassembled such that their component parts can be replaced when necessary. However, disassembly and replacement of the parts used with the assembly can be tedious, difficult and time consuming. Also, piecemeal replacement of valve assembly parts necessitates large inventories to ensure an adequate supply of each component of the assembly. The resulting cost is large.

Some prior art devices provide disposable assemblies, including disposable filters. Such devices are, however, inefficient inasmuch as it is usually necessary to replace the filter before replacement of the entire assembly is required. Since the filter comprises a small portion of the entire assembly, devices which propose disposal of the assembly at each instance when the filter needs replacement are expensive and, consequently, inefficient.

Also, in the field of liquid chromatography there are numerous manufacturers providing chromatographic equipment. The equipment of each manufacturer is generally not compatible with that of any other manufacturer. A typical user has numerous chromatographs provided by several different manufacturers. Accordingly, the typical user must further increase his inventory to maintain a separate supply of spare parts for each manufacturer's equipment. It is readily understood that since each manufacturer's valve assemblies are constructed differently, difficulty in replacing worn parts is increased due to the need to know the exact construction of valves for various manufacturers.

It is, therefore, desirable to provide a disposable valve assembly for a liquid chromatograph wherein the filter thereof can be replaced and the assembly reused until other components of the valve assembly must be replaced. It is further desirable to provide a valve assembly for a liquid chromatograph wherein the filter thereof may be quickly and easily replaced. It is additionally desirable to provide a valve assembly for a liquid chromatograph, which assembly is suitable for use with chromatographs made by various manufacturers.

SUMMARY OF THE INVENTION

These and other objects of the invention are met by providing a disposable check valve assembly for a liquid chromatograph pump. The valve assembly includes a valve subassembly for regulating the flow of the mobilizing liquid. The valve subassembly includes a spherical ball, a housing for receiving the ball and a valve seat against which the ball is seatable inside the housing. The seat and the housing include apertures which define a liquid flow path through the valve subassembly. A case is provided for receiving the valve subassembly. The case has a tapered end portion and an aperture in flow communication with the flow path of the valve subassembly. An end seal is provided which has a tapered end that is mountable upon the tapered end portion of the end cap. The end seal has an aperture which is positioned in flow communication with the flow path of the valve subassembly. A filter is fixedly positioned within the aperture of the end seal. The end seal with filter is removably attached to the end cap for easy replacement as needed.

In an alternative embodiment, two identical valve subassemblies are provided as described above. A spacer is positioned intermediate the two subassemblies and includes an aperture which is aligned with the flow path of the two subassemblies.

BEST MODE FOR CARRYING OUT THE INVENTION

Figure 1:
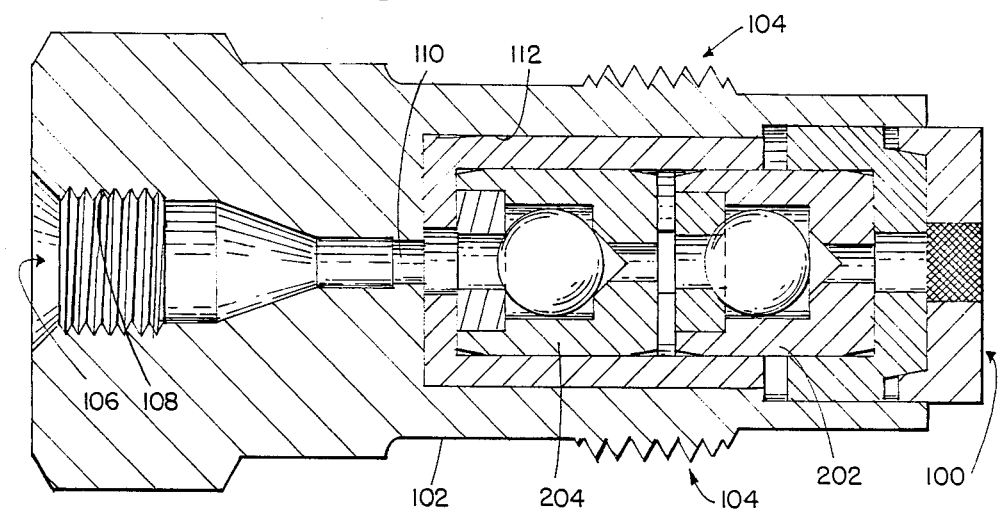
FIG. 1 is a side elevational sectional view of a disposable check valve assembly according to the present invention mounted in a cartridge holder.

As mentioned above, the present invention is directed toward a disposable check valve assembly for use in liquid chromatographs. The valve assembly which is the subject of the present invention is shown generally in FIG. 1 as a check valve 100 which is mounted in a cartridge holder 102.

The cartridge holder 102 includes a threaded surface 104 for securing the check valve 100 to a pump. The cartridge holder further includes a longitudinal channel 106 therethrough which has a threaded end portion 108, an interior portion 110 and an enlarged chamber end portion 112. The threaded end portion 108 is provided for receiving tubing or other apparatus adapted to provide the mobilized sample. The interior portion 110 defines a flow path through the chamber end portion in which the check valve is positioned, as will be discussed in detail below.

Figure 2:
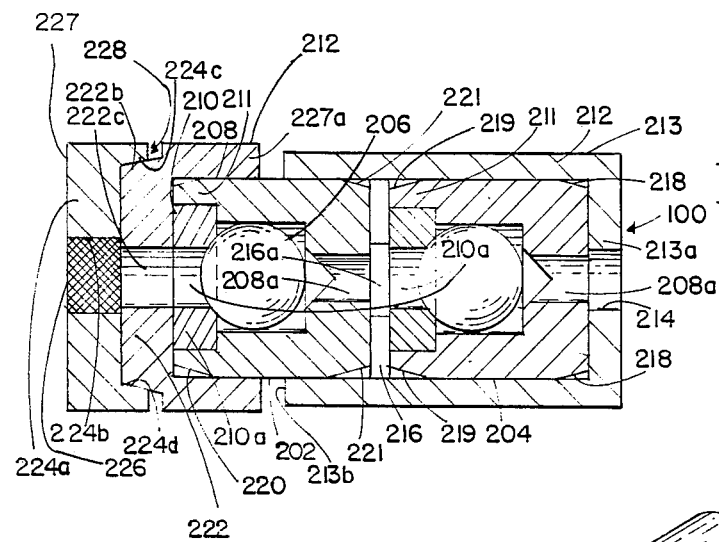
FIG. 2 is a side elevational sectional view of the disposable valve assembly of FIG. 1 shown with a reverse orientation.

With reference to FIG. 2, a more detailed explanation of the check valve 100 will be provided. The check valve 100 includes identical valve subassemblies 202 and 204. Each valve subassembly is provided for regulating the flow of the mobilized sample as is known in the art. Each valve subassembly includes a spherical ball 206 and a housing 208 for receiving the ball 206. Each subassembly further includes a valve seat 210 against which the ball 206 is seatable within the housing 208. The seat 210 has an aperture 210a and the housing 208 has an aperture 208a which together define a flow path for the mobilized liquid.

The seat 210 is adapted to fit securely within an open end 211 of the housing 208 such that the open end of the housing is flush with an outward facing face of the seat 210. It will be appreciated by those skilled in the art that the aperture 208a of the housing 208 is preferably shaped so as not to sealably seat the ball 206 and thereby allow fluid flow at times when the flow moves the ball 206 into position proximate the aperture 208a and remote from the aperture 210a of the seat 210. Likewise, it is desirable that the aperture 210a of the seat 210 be circular in shape to sealably seat the ball 206 and thereby interrupt the flow of liquid at times when the flow moves the ball 206 into position proximate the aperture 210a of the seat 210 and remote from the aperture 208a of the housing 208.

In the preferred embodiment, the housing 208 and the seat 210 are both generally cylindrical in shape. However, those skilled in the art will appreciate that any shape for the housing 208 and the seat 210 may be provided for the valve subassembly. In a particularly preferred embodiment, the spherical ball 206 is comprised of a ruby material and the seat 210 is comprised of a sapphire material. However, other suitable materials may be substituted for the ball 206 and the seat 210, as will be readily appreciated by those skilled in the art.

A cylindrical casing 212 is provided for securely receiving both valve subassemblies. The casing 212 includes a body 213 with a closed end 213a and an open end 213b through which the valve subassemblies are inserted upon assembly. The casing 212 has an end cap 222 positioned at the open end 213b of the body 213. As shown in FIG. 2, the body 213 is adapted to snugly receive one valve subassembly 204 entirely therein and to snugly receive a substantial portion of the second valve subassembly 202. It will be noted that the subassemblies 202 and 204 each include beveled edges 218, 219, 220 and 221 which facilitate their insertion into the body 213.

The body 213 has an aperture 214 in its closed end 213a which is adapted to be in flow communication with the encased valve subassemblies 202 and 204, and the interior portion 110 of the cartridge holder channel 106. A spacer 216 is provided intermediate the valve subassemblies. The spacer 216 also includes an aperture 216a which is aligned with the flow path as defined by the two subassemblies 202 and 204.

The end cap 222 has a collar portion 222a with an open end for securely receiving the exposed portion of valve subassembly 202 therein. The end cap 222 further has an end wall 222b with an aperture 222c with the aperture 222c being adapted to be in alignment with the flow path defined by the valve subassemblies 202 and 204. The perimeter of the end wall 222b of the end cap 222 is tapered outwardly such that an end seal 224 is readily mountable thereon.

The end seal 224 includes an end wall 224a with an aperture 224b therein for receiving a filter 226. The aperture 224b is in alignment with the flow path defined by the subassemblies 202 and 204. The end seal 224 also includes a collar portion 224c with an open end which has an inwardly tapered surface portion 224d matably mountable upon the correspondingly tapered end wall 222b of the end cap 222. The collar portion 224c and end wall 222b are sized and angled so that the end seal 224 may be snapped in place on the end cap 222 and selectively removed using the force supplied by the user's fingers without use of tools. Further, the fit is secure enough so that the end seal 224 will not fall off under its own weight and any weight the subassemblies 202 and 204 might apply thereto when the casing 212 is inverted with the open end 213b of the body 213 facing downward for insertion into or removal from the cartridge holder 102, or for insertion or removal of the cartridge holder into or from the pump head (not shown) with the check valve 100 therein. The perimeter of the end wall 222b and the correspondingly angled tapered surface portion 224d of the end seal 224 have matching shallow angles to provide the necessary frictional holding force but yet not hold the end cap so tightly that it cannot be removed by hand when desired to replace the end cap when the filter 226 is clogged and in need of replacement.

It will be noted by those skilled in the art that the end seal 224 is mounted upon the end cap 222 in a manner to provide a circumferential notch or gap 228 between the collar portion 224c of the end seal and collar portion 222a of the end cap. The notch 228 provides a gripping edge which facilitates quick and easy removal of the end seal 224 by the fingers of the user for replacement of a new end cap with a clean filter 226. As noted above, the advantage of the present method of mounting the filter 226 resides in the mating tapered surfaces of the end cap 222 and the end seal 224. The tapered surfaces allow for quick mounting using finger pressure to secure the end seal with filter to the check valve assembly such that the assembly may be easily placed in the cartridge 100 (FIG. 1) and secured to the chromatograph pump. This is true even in instances when the check valve 100 and/or the cartridge holder 102 are turned to an incline or upside down during assembly with the chromatograph pump.

Figure 3:
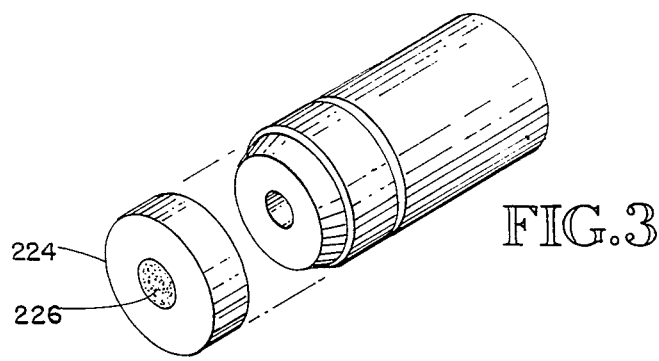
FIG. 3 is a partially exploded, perspective view of the valve assembly of FIG. 1 with the end seal filter shown removed.

The partially exploded perspective view of FIG. 3 illustrates the manner in which the end seal 224 is removed for replacement with a new end seal having a clean filter 226. The providing of a new filter is thus accomplished at very minimal expense and effort, unlike with prior art check valve assemblies where the entire check valve was disposed of simply because the filter was clogged.

It will be appreciated by those skilled in the art that the valve assembly of FIG. 2 is adapted to enable fluid to flow through the filter 226 and to the aperture 214 of the casing 212, and to inhibit fluid flow from the aperture 214 to the filter 226. It may be, however, desirable to re-orient the valve subassemblies 202 and 204 such that the fluid is enabled to flow from the aperture 214 to the filter 226 and inhibited from flowing from the filter 226 to the aperture 214.

While the presently preferred embodiment of the subject invention has been disclosed in detail herein, it will be appreciated by those skilled in the art that many modifications and variations thereof may be made without departing from the true scope and spirit of the invention. It is the intent of the inventor, by the appended claims, to embody all such modifications and variations.

I claim:

1. A check valve assembly for pumps used in liquid chromatography, comprising:

valve means for regulating the flow of the liquid, said valve means comprising a first valve subassembly including a spherical ball, a housing for receiving said ball and a valve seat against which said ball is seatable in said housing, said seat and said housing having apertures which define a liquid flow path through said valve means;

a case for receiving said valve means, said case having a tapered end portion;

an end seal having a tapered end removably mountable upon said tapered end portion of said case, said end seal having an aperture positioned to be in flow communication with the flow path of said valve means; and a filter fixedly positioned within said end seal aperture.

2. Apparatus as recited in claim 1 wherein said tapered end portion of said case frictionally holds said end seal with sufficient force to support the weight of said end seal and filter in place when the check valve assembly is turned with said end seal downward, but without sufficient force to prevent easy removal of the end seal by hand without tools.

3. Apparatus as recited in claim 1 wherein said end seal includes an edge portion adjacent said tapered end thereof and positioned such that when said end seal is mounted on said tapered end portion of said case the edge portion of said end seal provides an accessible gripping edge.

4. Apparatus as recited in claim 1 wherein said valve means further includes a second valve subassembly comprising a spherical ball, a housing for receiving said ball and a valve seat against which said ball is seatable in said housing, said seat and said housing having apertures which define a liquid flow path through said second valve subassembly, said valve means further including a spacer disposed between said first and second valve subassemblies, said spacer having an aperture and being positioned intermediate said first and second valve subassemblies such that the aperture of said spacer is in flow communication with the flow path defined by said first and second valve subassemblies.

5. Apparatus as recited in claim 4 wherein said case comprises an end cap and a body, said end cap having said tapered edge portion and an aperture positioned to be in flow communication with the flow path of said valve means, said body having an end wall positioned distal from said end cap with an aperture positioned in flow communication with the flow path of said valve means, an interior chamber for sealably receiving said first and second valve subassemblies therein, and an open end beyond which an extension portion of said valve means extends outward of said body, said end cap being sealably mountable to said extension portion of said valve means.

6. Apparatus as recited in claim 5 wherein said housing of said first and second valve subassemblies has beveled edges to facilitate insertion of said valve means into said casing upon assembly.

7. A check valve assembly for liquid chromatograph pumps, comprising:

valve means for regulating the flow of the liquid, said valve means including:

a spherical ball;

a generally cylindrical valve housing having first and second ends and an inner chamber for receiving said ball, said housing including an annular end wall with a center aperture at said first end which provides an outlet for the liquid and a circular aperture with an interior shoulder at said second end which provides an inlet for the liquid;

a disk shaped annular seat adapted to rest securely in the aperture against the shoulder of said valve housing such that the exteriorly facing surface of said seat is substantially flush with said second end of said housing, said seat having a circular center aperture therein against which said ball is seatable;

a generally cylindrical casing having an inside diameter substantially equal to the outside diameter of said valve housing for sealably receiving said valve housing therein, said casing having an apertured first end which provides an outlet for the liquid and an open second end for receiving said valve housing such that said second end of said valve housing extends beyond said second end of said casing; and an end cap having a first end sealably mountable to said second end of said valve housing, and a second end having a tapered perimeter sidewall and a central aperture adapted to be in liquid flow communication with said aperture of said valve seat; and an end seal for sealing a filter to said end cap, said end seal having a tapered interior wall at a first end mountable to the tapered perimeter sidewall of said end cap and an apertured second end, said seal having a central aperture at said second end for receiving a filter therein and adapted to be in flow communication with said aperture of said end cap second end when said end seal is mounted upon said end cap, the tapered interior wall of said end seal having a mating taper with the taper of said perimeter sidewall of said end cap to provide a frictional fit to hold said end seal with sufficient force to support the weight of said end seal and filter in place when the check valve assembly is turned with said end seal downward on insertion or removal of the check valve assembly from a pump, but without sufficient force to prevent easy removal of the end seal by hand without tools, thus removably coupling said end seal to said end cap.

* * * * *